United States Patent
Tsubata (10) Patent No.: US 8,483,978 B2
(45) Date of Patent: Jul. 9, 2013

(54) SYSTEM AND METHOD FOR MEASURING DAMAGE LENGTH

(75) Inventor: Hiroyuki Tsubata, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 361 days.

(21) Appl. No.: 13/024,102

(22) Filed: Feb. 9, 2011

(65) Prior Publication Data

US 2011/0196622 A1   Aug. 11, 2011

(30) Foreign Application Priority Data

Feb. 9, 2010   (JP) .................................. 2010-026163
Feb. 4, 2011   (JP) .................................. 2011-022941

(51) Int. Cl.
*G06F 19/00* (2011.01)
(52) U.S. Cl.
USPC .............. 702/39; 702/35; 702/56; 702/182; 250/227.14; 250/227.16; 250/227.23; 250/227.18; 73/593; 340/870.16
(58) Field of Classification Search
USPC ............... 702/39, 35, 56, 182; 250/227.14, 250/227.16, 227.15, 237 R, 237 G, 227.23, 250/227.18; 73/593, 659, 660, 602, 862.08; 340/870.16, 635
See application file for complete search history.

(56) References Cited

U.S. PATENT DOCUMENTS

| | | | | |
|---|---|---|---|---|
| 5,511,422 A | * | 4/1996 | Hernandez | 73/593 |
| 5,898,502 A | * | 4/1999 | Horiuchi et al. | 356/416 |
| 6,053,047 A | * | 4/2000 | Dister et al. | 73/593 |
| 6,297,742 B1 | * | 10/2001 | Canada et al. | 340/635 |
| 6,331,823 B1 | * | 12/2001 | El-Ibiary | 340/870.16 |
| 6,498,992 B1 | * | 12/2002 | Toyota et al. | 702/35 |
| 6,525,308 B1 | * | 2/2003 | Schmidt-Hattenberger | 250/227.23 |
| 6,526,829 B1 | * | 3/2003 | Lysen et al. | 73/593 |
| 6,546,814 B1 | * | 4/2003 | Choe et al. | 73/862.08 |
| 6,694,285 B1 | * | 2/2004 | Choe et al. | 702/182 |
| 7,231,303 B2 | * | 6/2007 | Griessler et al. | 702/34 |
| 7,470,888 B2 | * | 12/2008 | Ogisu et al. | 250/227.14 |
| 7,640,802 B2 | * | 1/2010 | King et al. | 73/489 |
| 7,663,502 B2 | * | 2/2010 | Breed | 340/12.25 |
| 8,065,916 B2 | * | 11/2011 | Yanohara et al. | 73/593 |
| 2005/0067559 A1 | * | 3/2005 | Ogisu et al. | 250/227.14 |
| 2006/0152735 A1 | * | 7/2006 | Kageyama et al. | 356/483 |
| 2007/0200057 A1 | * | 8/2007 | Ogisu et al. | 250/227.14 |

FOREIGN PATENT DOCUMENTS

JP   2008-139171   6/2008

* cited by examiner

*Primary Examiner* — Carol Tsai
(74) *Attorney, Agent, or Firm* — Konomi Takeshita (57) ABSTRACT

The damage length measurement system has an object being measured that comprises a plurality of members is vibrated by an oscillator, and the vibration that propagates through the object being measured is detected by three sensors. A measurement apparatus analyzes that vibration wave, and measures the arrival time of the maximum peak. Using the fact that the time for a wave to propagate between two vibration detection sensors separated by a set interval is fixed, the measurement apparatus determines whether the difference in arrival time between two sensors is within a set reference range that includes the vibration propagation time between two vibration sensors. When the measurement apparatus determines that the difference is not within the set reference range, uses the fact that that wave is delayed compared to the wave that was to be detected.

4 Claims, 4 Drawing Sheets

SYSTEM AND METHOD FOR MEASURING DAMAGE LENGTH

CROSS REFERENCE TO RELATED APPLICATIONS

This application claims priority under 35 U.S.C. 119 based upon Japanese Patent Application Serial No. 2010-026163, filed on Feb. 9, 2010, and Japanese Patent Application Serial No. 2011-022941, filed on Feb. 4, 2011. The entire disclosures of the aforesaid applications are incorporated herein by reference.

FIELD OF THE INVENTION

The present invention relates to a damage length measurement system and damage length measurement method that measure damage length by placing an oscillator and vibration detection sensors on an object being measured, measures the time of arrival of vibration that propagates through the object being measured from the oscillator to the vibration detection sensors and measures the damage length based on the delay in this arrival time compared with the case when there is no damage.

BACKGROUND OF THE INVENTION

Figure 3A:
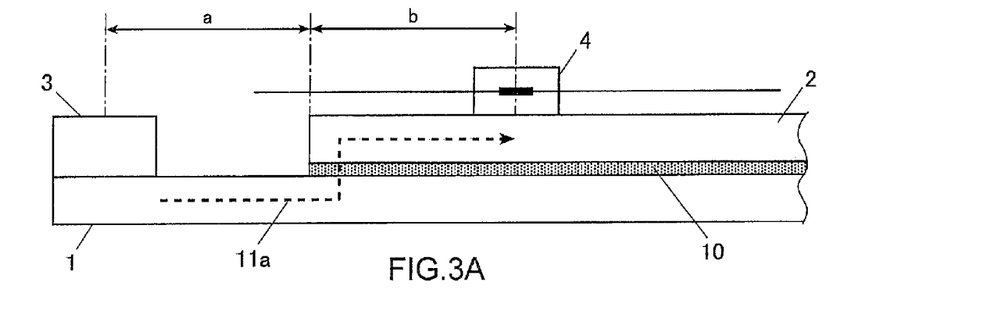
FIGS. 3A to 3C are diagrams for explaining the fundamental principles of damage length measurement.
Figure 3B:
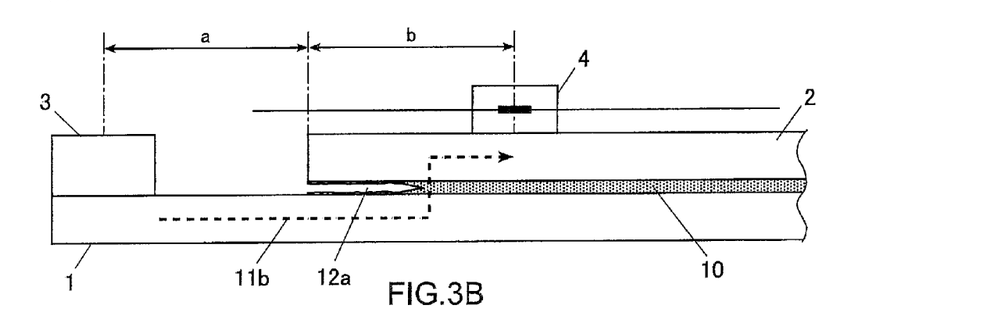
Figure 3C:
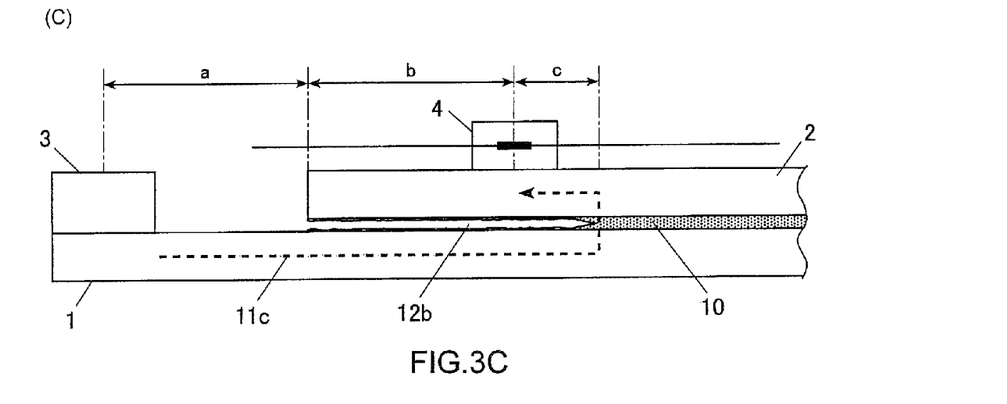

As illustrated in FIGS. 3A, 3B, 3C, it is possible to measure the damage length of an object to be measured that is made by adhering a member 1 and member 2. In FIGS. 3A, 3B, 3C, an oscillator 3 made from a piezo element or the like is placed on the member 1, and a vibration detection sensor 4 such as an FBG (Fiber Bragg Grating) optical fiber sensor is placed on the member 2. The object being measured is vibrated by the oscillator 3, and the arrival time of the vibration that propagates through the object being measured from the oscillator 3 to the vibration detection sensor 4 is measured. Measurement of the arrival time is first performed for an object having no damage as a calibration as illustrated in FIG. 3A. In this case, vibration (elastic wave) propagates along a vibration propagation path 11$a$ as illustrated in FIG. 3A from the oscillator 3 to the vibration detection sensor 4. The arrival time of this vibration is recorded.

Next, as the actual measurement, the oscillator 3 and vibration detection sensor 4 are placed, as a rule, in the same positions on the object to be measured, which has the same construction as the object above, however for which it is unknown whether or not there is damage, as illustrated in FIGS. 3B and 3C, and the arrival time is measured (in the case that the oscillator 3 and vibration detection sensor 4 are not placed in the same position, the propagation time for that difference is subtracted). As illustrated in FIG. 3B, when there is damage in the form of peeling 12$a$ occurring on an adhesion layer 10, vibration propagates along the vibration propagation path such as illustrated in the figure, however, the peeling 12 does not extend to underneath the vibration detection sensor 4, so there is hardly any effect on the arrival time of the vibration. However, as illustrated in FIG. 3C, when there is peeling 12$b$ that extends to underneath the vibration detection sensor 4, vibration propagates along the vibration propagation path 11$c$ as illustrated in the figure and goes around the peeling, so there is a delay in the arrival time of the vibration. Therefore, by calculating the difference between the arrival time during actual measurement and the arrival time during calibration, it is possible to determine whether or not peeling has extended to underneath the vibration detection sensor 4. Furthermore, when peeling has extended to underneath the vibration detection sensor 4, it is possible to calculate the peeling length as will be explained below.

As illustrated in FIGS. 3A to 3C, the distance from the end section of the adhesion layer 10 between oscillator 3 and the vibration detection sensor 4 to the oscillator 3 is taken to be "a", and the distance to the vibration detection sensor 4 is taken to be "b". The distances "a" and "b" are known values. When it is determined that peeling has extended to underneath the vibration detection sensor 4 due to the occurrence of a delay in the arrival time, the length of peeling that further extends from the vibration detection sensor 4 is taken to be distance "c" as illustrated in FIG. 3C. The peeling length to be found is (b+c). The delay of the arrival time is taken to be $\Delta t$. The difference between the propagation distance along the vibration propagation path 11$a$ and the propagation distance along the vibration propagation path 11$c$ is (2×c). Therefore, when the group velocity of vibration is taken to be V, $\Delta t=(2\times c)/V$, and this equation can be transformed to $c=(V\times\Delta t)/2$. Therefore, c can be found by entering the measured $\Delta t$ into the equation above, and the peeling length is found as $(b+c)=(b+(V\times\Delta t)/2)$.

Figure 4A:
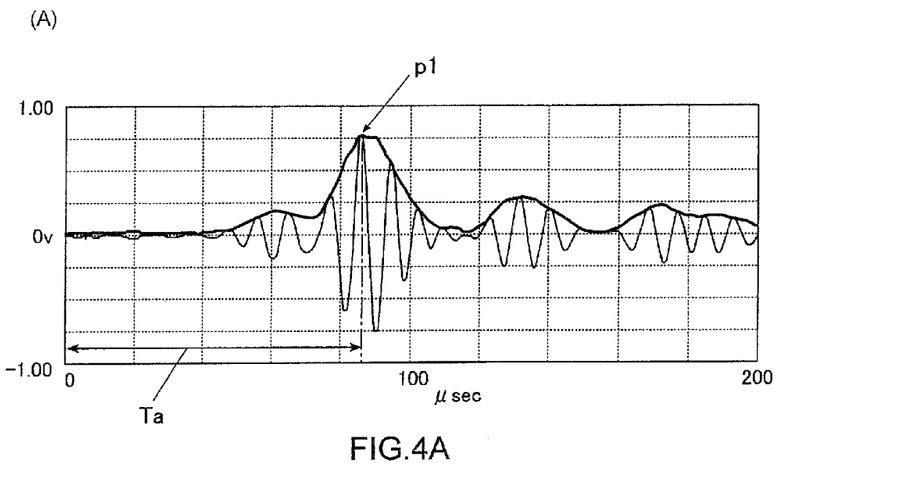
FIGS. 4A and 4B are diagrams illustrating the vibration waveform that is detected by a vibration detection sensor and analyzed by a measurement apparatus.
Figure 4B:
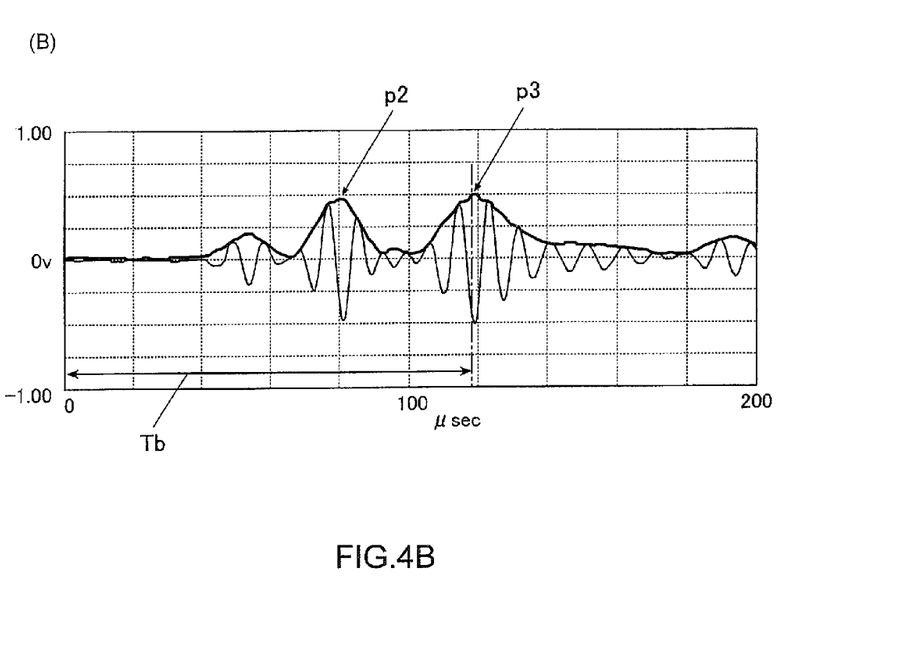

Analysis of the vibration detected by the vibration detection sensor 4 can be performed by a wave motion analysis apparatus that uses an optical filter such as disclosed in Japanese Patent Application Publication No. 2008-139171. By processing a detected wave motion signal, it is possible to acquire the change in time of the vibration as illustrated in FIGS. 4A and 4B, and to identify the peak of the vibration. By calculating the delay of the arrival time due to the shifting over time of the maximum peak, the damage length can be measured as described above.

In the case of a vibration waveform as illustrated in FIG. 4A, the reliability of the estimation of the damage length based on the arrival time Ta of the maximum peak p1 is high. However, depending on the state of the damage, a plurality of waves, such as reflected waves, overlap the vibration waveform as illustrated in FIG. 4B. Therefore, the maximum peak p3 occurs in a different location than the peak p2 that is originally supposed to be obtained, and the damage length estimated based on that arrival time Tb may be wrong. Conventionally, it could not be determined whether the maximum peak p3 was a peak due to the delay of the vibration as theoretically explained using FIGS. 3A to 3C, or was a peak that became high due to some other reason such as reflection. Therefore, there is a possibility that it will be determined that damage has occurred due to erroneous measurement.

SUMMARY OF THE INVENTION

Considering the above situation, the purpose of the present invention is to provide a damage length measurement system and damage length measurement method capable of measuring damage length with high reliability and accuracy.

In order to solve the problems above, according to a first embodiment of the present invention there is provided a damage length measurement system for measuring a length of damage that occurred in an object being measured, the system comprising:

an oscillator that applies an ultrasonic vibration to the object;

a plurality of vibration detection sensors at mutually different positions that detect a vibration wave that propagates through the object from the oscillator; and a measurement apparatus that controls the vibration of the oscillator, and analyzes the vibration wave that was detected by the vibration detection sensors by means of processing detected signals from the vibration detection sensors, wherein the measurement apparatus is constructed such that it:

(1) executes a process of calculating arrival times of maximum peaks of the vibration wave detected by at least two vibration detection sensors that are selected from the plurality of vibration detection sensors, and calculating a difference between the arrival times;

(2) executes a process, following process (1), of determining whether or not the difference between the selected sensors is within a set reference range considering a vibration propagation time between the at least two vibration sensors;

(3) executes a process, when it is determined in process (2) that the difference is within the reference range, of calculating the damage length based on a delay time with respect to a calibration value of the arrival times of the maximum peaks;

(4) executes a process, when it is determined in process (2) that the difference is not within the reference range, of detecting a peak that arrived before the maximum peak and has a specified vibration amplitude or greater for at least one of the at least two vibration detection sensors related to the difference; and (5) executes a process, when the peak having the specified vibration amplitude or greater is detected in process (4), of replacing the arrival time of the maximum peak with the arrival time of that peak and calculating the difference in the process (1), and then executing processes (2) and (3).

According to a second embodiment of the present invention, there is provided the damage length measurement system according to embodiment 1, wherein the measurement apparatus is constructed such that:

in process (1) it calculates the difference between the maximum peak of the vibration wave detected by a specified vibration sensor and the maximum peak of the vibration wave detected by each of the other vibrations sensors in process (2) it determines whether or not each difference is within the reference range; and in process (4), when none of the differences is within the reference range, for the specified vibration detection sensor, it detects a peak that arrived before the maximum peak and that has the specified vibration amplitude or greater.

According to a third embodiment of the present invention, there is provided a damage length measurement method for measuring a length of damage that occurred in an object being measured, the method comprising the steps of:

applying an ultrasonic vibration to the object by an oscillator;

detecting at mutually different positions a vibration wave that propagates through the object from the oscillator by a plurality of vibration detection sensors; and executing a measurement process of controlling the vibration of the oscillator, and analyzing the vibration wave that was detected by the vibration detection sensors by means of processing detected signals from the vibration detections sensors, wherein the measurement process:

(1) executes a process of calculating arrival times of maximum peaks of the vibration wave detected by at least two vibration detection sensors that are selected from the plurality of vibration detection sensors, and calculating a difference between the arrival times;

(2) executes a process, following process (1), of determining whether or not the difference between the selected sensors is within a set reference range considering a vibration propagation time between the at least two vibration sensors;

(3) executes a process, when it is determined in process (2) that the difference is within the reference range, of calculating the damage length based on a delay time with respect to a calibration value of the arrival times of the maximum peaks;

(4) executes a process, when it is determined in process (2) that the difference is not within the reference range, of detecting a peak arrived before the maximum peak and that has a specified vibration amplitude or greater for at least one of the at least two vibration detection sensor related to the difference; and (5) executes a process, when the peak having the specified vibration amplitude or greater is detected in process (4), of replacing the arrival time of the maximum peak with the arrival time of that peak and calculating the difference in the process (1), and then executing processes (2) and (3).

According to a fourth embodiment of the present invention there is provided the damage measurement method according to embodiment 3, wherein the method uses three or more vibration detection sensors, and the measurement process:

in process (1) calculates the difference between the maximum peak of the vibration wave detected by a specified vibration sensor and the maximum peak of the vibration wave detected by each of the other vibrations sensors in process (2) determines whether or not each difference is within the reference range; and in process (4), when none of the differences is within the reference range, for the specified vibration detection sensor, detects a peak that arrived before the maximum peak and that has the specified vibration amplitude or greater.

With the present invention, damage length is calculated based on a vibration wave that is detected by a plurality of vibration sensors. Therefore, by calculating the average value, it is possible to measure damage length with high precision. Thus, in the case where a maximum peak is obtained and the peak is high due to another reason such as reflection, it is an error about detecting the peak, and that may cause an error in measuring the damage length. The present invention utilizes the fact that the time for an elastic wave to propagate between two vibration detection sensors separated by a set distance is fixed. Therefore whether or not there is inconsistency in the arrival times is determined. Also, a reflected wave goes around the damage, so the wave is delayed compared with a wave that arrives directly. Using this, the arrival time of a peak that arrives before the maximum peak is used in calculation. In other words, with the present invention, whether or not the difference in arrival time between two sensors is within a predetermined reference time range that includes the vibration propagation time between two vibration sensors is determined. When the difference is within the reference range, calculation can be performed correctly. When the difference is not within the reference range, measurement can be performed with high precision by correcting the error in peak detection by replacement with a peak that arrives before the maximum peak and has a specified vibration amplitude or greater. In other words, the invention has the advantage of being able to improve reliability of the measurement value.

Other features and advantages of the present invention will become apparent from the following detailed description, taken in conjunction with the accompanying drawings, which illustrate, by way of example, the principles of the invention.

DETAILED DESCRIPTION OF THE INVENTION

In the following, a preferred embodiment of the present invention will be described in detail with reference to the accompanying, exemplary diagrams. The following is an embodiment of the present invention, however does not limit the present invention.

Figure 1:
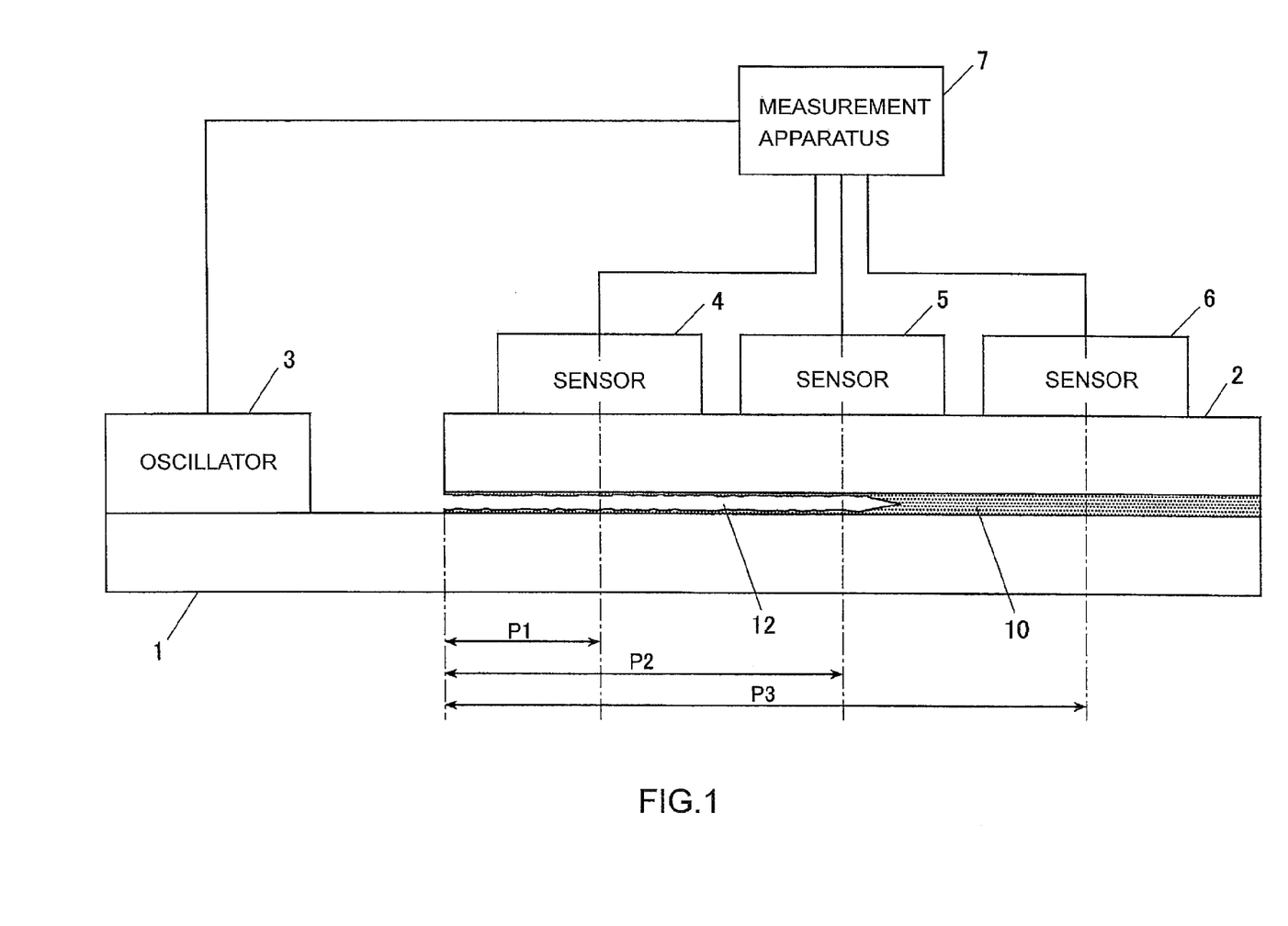
FIG. 1 is a diagram illustrating an object being measured and the damage length measurement system of an embodiment of the present invention.

As illustrated in FIG. 1, the damage length measurement system of this embodiment is for measuring an object that joins a member 1 and a member 2. The damage length measurement system of this embodiment comprises an oscillator 3, three vibration detection sensors 4, 5 and 6, and a measurement apparatus 7. The oscillator 3 is provided in order to apply an ultrasonic vibration to the object being measured, and is a piezo element. The oscillator 3 is placed on the member 1. The vibration detection sensors 4, 5 and 6 are FBG (Fiber Bragg Grating) optical fiber sensors. The vibration detection sensors 4, 5 and 6 are placed on the member 2. The vibration detection sensors 4, 5 and 6 are arranged in the order vibration detection sensor 4, vibration detection sensor 5 and vibration detection sensor 6 toward the inward direction from the end section of the adhesion layer 10 between member 1 and member 2. The distances from the end of the adhesion layer 10 to each of the vibration detection sensors 4, 5 and 6 are in order, P1, P2 and P3. The measurement apparatus 7 controls the vibration from the oscillator 3, analyzes the vibration wave detected by each of the vibration detection sensors 4, 5 and 6 by processing the detection signals from the vibration detection sensors 4, 5 and 6, and calculates the damage length.

Figure 2:
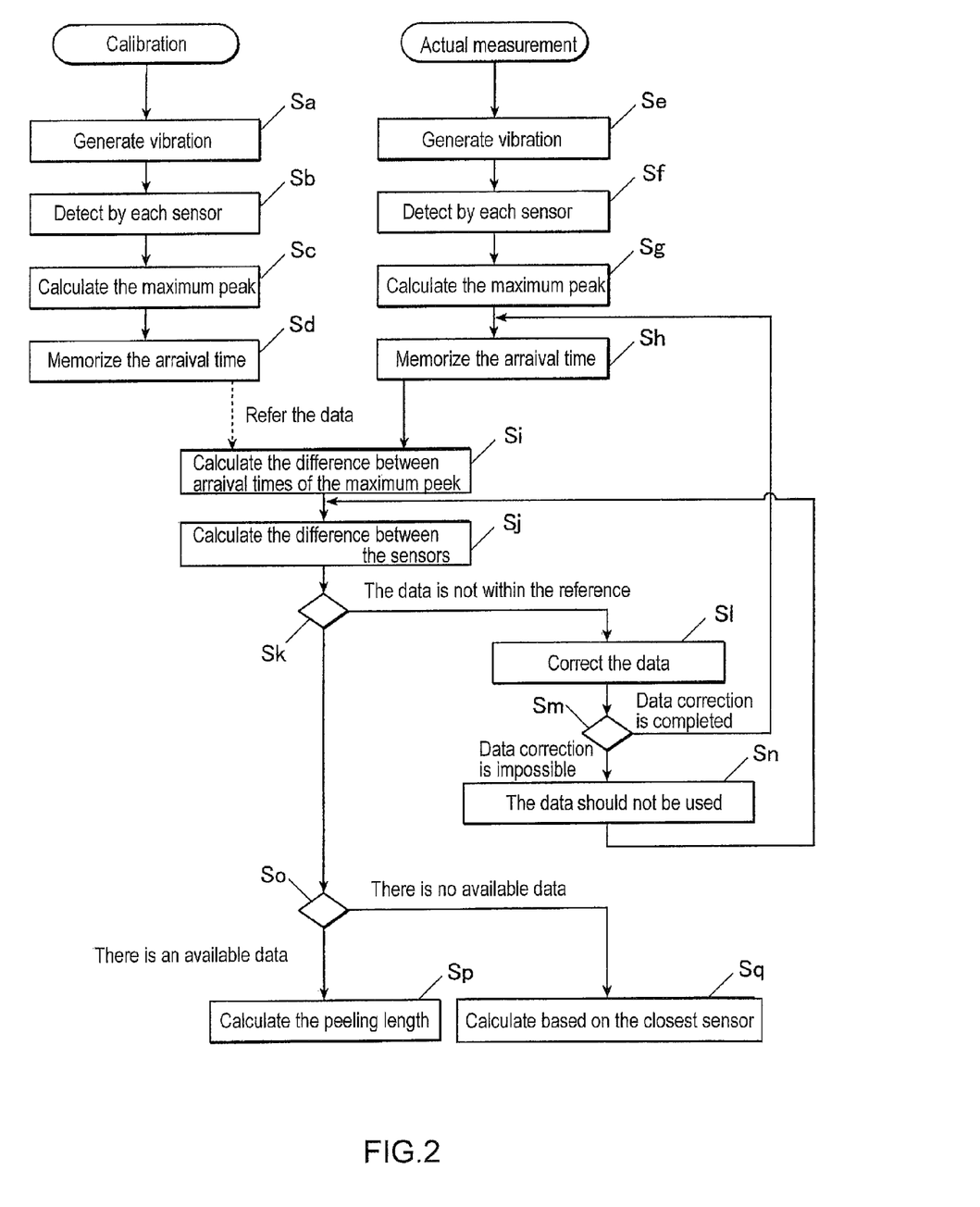
FIG. 2 is a flowchart illustrating the processing flow of the damage length measurement system and damage length measurement method of an embodiment of the present invention.

The measurement apparatus 7, first executes a calibration process comprising processing steps Sa to Sd as illustrated in the flowchart in FIG. 2. Calibration is performed on an object to be measured that has no damage and that comprises members 1 and 2 and adhesion layer 10, with the arrival time of the maximum peak of the vibration wave that propagates through this undamaged object being recorded as the calibration value.

In the calibration process, first, in order to start measurement, the measurement apparatus 7 controls the oscillator 3 to generate vibration from the oscillator 3 (process step Sa), while at the same time acquires the vibration wave detected by each of the vibration detection sensors 4, 5 and 6 (process step Sb). In other words, is process Sb, the measurement apparatus 7 converts the change over time of the output values from the vibration detection sensors 4, 5 and 6 to numerical data. In visualizing that data, waveforms as illustrated in FIGS. 4A, 4B are obtained. Next, the measurement apparatus 7 calculates and finds the maximum peak of each vibration wave (process step Sc). That method is not limited, for example, the maximum peaks are found by performing Hilbert transformation on the vibration wave data. Next, the measurement apparatus 7 identifies the time from the start of measurement at which the peak of the vibration wave becomes the maximum as the arrival time of the maximum peak of the vibration wave, and stores that value in an internal memory or the like (process step Sd). This recorded value becomes the calibration value. Calibration then ends.

Next, the following describes the actual measurement that includes process steps Se to Sq as shown in the flowchart in FIG. 2. By this damage length measurement system, it is possible to measure a damage length in the same structure which is composed of the members 1, 2 and the adhesion layer 10 when the calibration value for the structure is calculated and memorized. The oscillator 3 and the vibration detection sensors 4, 5, and 6 are located at the positions that are the same with that of calibration process. As described in the calibration process, the measurement apparatus 7 controls the oscillator 3 to generate vibration to start the measurement, and acquires the vibration waves detected by the vibration detection sensors 4, 5, and 6 (process step Sf). Next, the measurement apparatus 7 calculates to determine the maximum peaks in each of the vibration waves (process step Sg). Next, the measurement apparatus 7 identifies the time from the start of measurement at which the peak of the vibration wave becomes the maximum as the arrival time of the maximum peak of the vibration wave, and stores that value in the internal memory or the like (process step Sh). This recorded value corresponds to the measured value of the arrival time of the maximum peak of the vibration wave.

Next, the measurement apparatus 7 calculates a calibration difference which is the difference between the calibration value Tr that was recorded in process step Sd and the actual measurement value T that is recorded in process step Sh (process step Si). Here, in order to explain the theory, the calibration differences based on the values detected by each of the vibration detections sensors 4, 5 and 6 are taken in order to be $\Delta T1 = T1 - Tr2$, $\Delta T2 = T2 - Tr2$ and $\Delta T3 = T3 - Tr3$. Next, the measurement apparatus 7 calculates the difference in combinations of two values selected from the calibration differences $\Delta T1$, $\Delta T2$ and $\Delta T3$ calculated in process step Si, in other words $(\Delta T1 - \Delta T2)$, $(\Delta T2 - \Delta T3)$ and $(\Delta T3 - \Delta T1)$ (process step Sj). Process step Sg and this process step Sj correspond to process (1) above. Each of the differences, $(\Delta T1 - \Delta T2)$, $(\Delta T2 - \Delta T3)$ and $(\Delta T3 - \Delta T1)$, corresponds to the round trip vibration propagation times between vibration detection sensors.

Next, the measurement apparatus 7 determines whether or not the differences between sensors $(\Delta T1 - \Delta T2)$, $(\Delta T2 - \Delta T3)$ and $(\Delta T3 - \Delta T1)$ are within a set reference range (process step Sk, corresponds to process (2) above). The set reference range is a reference range that includes the vibration propagation time between two vibration detection sensors. The reference range will be explained here. Taking the vibration group velocity to be V, referencing FIGS. 3A to 3C, the peeling length according to the theoretical equation for the peeling length described above $(b + (V \times \Delta t)/2)$, becomes $(P1 + (V \times \Delta T1)/2)$ when $\Delta T1$ and P1 are used, becomes $(P2 + (V \times \Delta T2)/2)$ when $\Delta T2$ and P2 are used, and becomes $(P3 + (V \times \Delta T3)/2)$ when $\Delta T3$ and P3 are used. These peeling lengths are equal, so the three equations $(P1 + (V \times \Delta T1)/2) = (P2 + (V \times \Delta T2)/2)$, $(P2 + (V \times \Delta T2)/2) = (P3 + (V \times \Delta T3)/2)$ and $(P3 + (V \times \Delta T3)/2) = (P1 + (V \times \Delta T1)/2)$ are established. By transforming these three equations, $(\Delta T1 - \Delta T2) = 2(P2 - P1)/V$, $(\Delta T2 - \Delta T3) = 2(P3 - P2)/V$ and $(\Delta T3 - \Delta T1) = 2(P1 - P3)/V$. The right hand sides of these three equations become constants, and correspond to the round trip vibration propagation time between two vibration detection sensors. In other words, $2(P2-P1)/V$ corresponds to the round trip vibration propagation time through the object being measured between vibration detection sensors 4 and 5, $2(P3-P2)/V$ corresponds to the round trip vibration propagation time through the object being measured between vibration detection sensors 5 and 6, and $2(P1-P3)/V$ corresponds to the round trip vibration propagation time through the object being measured between vibration detection sensors 4 and 6. The wave propagation distance and the velocity are set, so become constants. With $2(P2-P1)/V$, $2(P3-P2)/V$ and $2(P1-P3)/V$ as reference values, the reference ranges that include each reference value are respectively set. Normally, the reference range is a numerical range having a specified width with the reference value as the center value. Depending on whether or not the differences between sensors based on actual measurement $(\Delta T1-\Delta T2)$, $(\Delta T2-\Delta T3)$ and $(\Delta T3-\Delta T1)$ are within the reference ranges, whether or not the maximum peak has been correctly detected can be determined with fixed reliability according to the specified width. When a difference is outside the reference range, there is a high possibility that the maximum peak obtained by the measurement apparatus 7 does not correspond to the same wave.

In process step Sk, the measurement apparatus 7 determines whether any of the differences between sensors that were detected in process step Sj are not within the reference range described above. When it is determined that there is a difference between sensors that is not within the reference range, the measurement apparatus 7 executes a data correction process for at least one of the vibration detection sensors related to the differences between sensors to detect a peak that arrived before the maximum peak and that has a specified vibration amplitude or greater (process step Sl).

For example, in process step Sk, when it is determined that the differences between sensors $(\Delta T1-\Delta T2)$ and $(\Delta T3-\Delta T1)$ are not within the respective reference ranges, and it is determined that the difference between sensors $(\Delta T2-\Delta T3)$ is within the respective reference range, there is a high probability that the problem is with $\Delta T1$. Therefore, in step Sl, the measurement apparatus 7 executes a correction process on the vibration wave that was detected by vibration detection sensor 4, and detects a peak having a specified vibration amplitude or greater and that arrived before the maximum peak. In this process, for example, when a half value of the maximum peak of vibration wave, that was determined as being not within the respective reference range, is set as the specified vibration amplitude, by searching, in a time period between the start of the measurement and the arrival time of the maximum peak, peaks having the specified vibration amplitude or greater, it is possible to replace the maximum peak with a peak that firstly appears in the search. Similarly, when there is a high probability that the problem is with $\Delta T2$, the measurement apparatus 7 performs the same process on the vibration wave that was detected by the vibration detection sensor 5, and when there is a high probability that the problem is with $\Delta T3$, performs the same process on the vibration wave detected by the vibration detection sensor 6. In this way, when there are three or more vibration detection sensors, if the difference between the maximum peak of a vibration wave detected by an identified vibration detection sensor (for example, vibration detection sensor 4) and the maximum peaks of the vibration waves detected by the other vibration detection sensors (for example, vibration detection sensors 5 and 6) are calculated and found to be not within the reference ranges, the measurement apparatus 7 determines that the vibration wave detected by the identified vibration detection sensor (for, example, vibration sensor 4) should be the object of the correction process.

When a peak that arrives before the maximum peak and that has a specified vibration amplitude or greater is detected in the step Sl, the measurement apparatus 7 performs correction by replacing the arrival time of the maximum peak with the arrival time of that peak. Moreover, in process step Sm, the measurement apparatus 7 determines that correction is "complete", then returns to process step Sh and executes processing starting from process step Sh using the newly corrected value.

In process step Sl, when it was not possible to detect even one peak that arrived before and had a specified vibration amplitude or greater, the measurement apparatus 7 determines in process step Sm that "correction is not possible" and advances to process step Sn. In process step Sn, the measurement apparatus 7 recognizes the calibration difference data that was detected by the specified vibration sensor that determined that "correction is not possible" as "unusable data", and returns to process step Sj. In process step Sj, the measurement apparatus 7 calculates the differences between sensors again for all the data except the calibration difference data that was recognized as "unusable data", and then executes the processes from process step Sk.

For example, in process step Sk, when it is determined that neither difference between sensors $(\Delta T1-\Delta T2)$ nor the difference between sensors $(\Delta T3-\Delta T1)$ are within the reference range, but that the difference between sensors $(\Delta T2-\Delta T3)$ is within the reference range, the measurement apparatus 7 executes processing for the vibration wave that was detected by the vibration sensor 4 in order to detect a peak that arrived before the maximum peak and that has a specified vibration amplitude or greater. As a result, when it was not possible to detect a peak that arrived before the maximum peak and that has a specified vibration amplitude or greater, the calibration difference $\Delta T1$ that was detected by vibration detection sensor 4 is not used, and the difference between sensors $(\Delta T2 \times \Delta T3)$ is calculated again using the calibration values $\Delta T2$ and $\Delta T3$ for the arrival times of the maximum peak of the vibration wave detected by the vibration detection sensors 5 and 6.

In this way, the calculation of the regressive processing from process step Sm to process step Sh, and the regressive processing from process step Sm to process step Sj via process step Sn is repeated until it is determined that there is no difference between sensors out of the reference range. In other words, processing is repeatedly executed until all of the remaining differences between sensors are within the reference range, or until there are no longer two or more "usable" calibration difference data remaining and recalculation is not possible.

In process step Sk, when it is determined that there are no differences between sensors out of the reference range, the measurement apparatus 7 advances to process step So. In process step So, the measurement apparatus 7 determines whether or not there are any differences between sensors that were determined to be within the reference range, or in other words, determines whether or not there is calibration difference data that was determined to be usable. When there is usable calibration difference data, the measurement apparatus 7 advances to process step Sp.

In process step Sp, the measurement apparatus 7 calculates the peeling lengths based on all of the usable calibration difference data, and also calculates the average peeling length.

For example, as described above, the calibration difference $\Delta T1$ that was detected by the vibration sensor 4 is recognized as "unusable data", and finally, in process step Sk, when it is determined that the difference between sensors ($\Delta T2-\Delta T3$) is within the reference range, the measurement apparatus 7 executes processing for the vibration wave detected by vibration sensors 5 and 6 and calculates the damage length based on the delay times $\Delta T2$ and $\Delta T3$ of the arrival times of the maximum peak with respect to calibration values. In other words, the measurement apparatus 7 uses the calibration differences $\Delta T2$ and $\Delta T3$ to calculate the peeling lengths from (P2+(V×$\Delta T2$)/2), (P3+(V×$\Delta T3$)/2), and outputs the average value as the measurement value.

On the other hand, when it is determined in process step So that there is no usable data, the measurement apparatus 7 advances to process step Sq and executes a process on the vibration wave that was detected by the vibration detection sensor 4 that is closest to the oscillator, and calculates the damage length based on the delay time $\Delta T1$ of the arrival time of the maximum peak with respect to the calibration value. In other words, using $\Delta T1$, the measurement apparatus 7 calculates the peeling length from (P1+(V×$\Delta T1$)/2), and outputs that value as the measurement value.

In the embodiment described above, an example was described for the case of three vibration detection sensors, however, needless to say, similar measurement is also possible for the case of four or more sensors.

Moreover, in the case of only two vibration detection sensors, for example vibration detection sensors 4 and 5, the processing from process step Sk on can be performed as described below.

In process step Sk, when the difference between sensors ($\Delta T1-\Delta T2$) is not within the reference range, in process step Sl, the measurement apparatus 7 executes processing on the at least one of the vibration wave detected by the vibrations detection sensors 4 and 5 in order to detect a peak that arrived before the maximum peak and has a specified vibration amplitude or greater. For example, when a peak could be detected in the vibration wave that was detected by vibration detection sensor 4 or vibration detection sensor 5 that arrived before the maximum peak and had a specified vibration amplitude or greater, the measurement apparatus 7 performs correction of the vibration wave that was detected by vibration detection sensor 4 or vibration detection sensor 5 in order to replace the arrival time of the maximum peak with the arrival time of the peak having a specified vibration amplitude or greater, then determines that "correction is complete" and returns to process step Sh, after which the measurement apparatus 7 executes process from process step Sh on based on the value of the arrival time of the newly correction maximum peak. When it was not possible to detect even one peak in the vibration wave that was detected by vibration detection sensor 4 or vibration detection sensor 5 that arrived before the maximum peak and had a specified vibration amplitude or greater, the measurement apparatus 7 determines that "correction is not possible", then advances to process step Sn, and recognizes the calibration difference data that was detected by vibration detection sensor 4 and vibration detection sensor 5 as "unusable data".

Furthermore, in the embodiment above, a case in which the tip end of damage exceeds the position of the vibration detection sensor 4, or in other words, the damage length is P1 or greater was explained. In theory, in the case where the damage length is less than P1, all of the calibration differences would become zero. Therefore, in FIG. 4, it is possible to provide a step after process step Si of determining whether or not all of the calibration differences are zero; and for convenience, when all of the calibration differences are zero, calculating that the damage length is P1 or zero, and then ending processing.

It is to be understood that the above-described embodiment is illustrative of only a few of the many possible specific embodiments which can represent applications of the principles of the invention. Numerous and varied other arrangements can be readily devised by those skilled in the art without departing from the spirit and scope of the invention.

What is claimed is:

1. A damage length measurement system for measuring a length of damage that occurred in an object being measured, the system comprising:
    an oscillator that applies an ultrasonic vibration to the object;
    a plurality of vibration detection sensors at mutually different positions that detect a vibration wave that propagates through the object from the oscillator; and
    a measurement apparatus that controls the vibration of the oscillator, and analyzes the vibration wave that was detected by the vibration detection sensors by means of processing detected signals from the vibration detection sensors,
    wherein the measurement apparatus is constructed such that it:
    (1) executes a process of calculating arrival times of maximum peaks of the vibration wave detected by at least two vibration detection sensors that are selected from the plurality of vibration detection sensors, and calculating a difference between the arrival times;
    (2) executes a process, following process (1), of determining whether or not the difference between the selected sensors is within a set reference range considering a vibration propagation time between the at least two vibration sensors;
    (3) executes a process, when it is determined in process (2) that the difference is within the reference range, of calculating the damage length based on a delay time with respect to a calibration value of the arrival times of the maximum peaks;
    (4) executes a process, when it is determined in process (2) that the difference is not within the reference range, of detecting a peak that arrived before the maximum peak and has a specified vibration amplitude or greater for at least one of the at least two vibration detection sensors related to the difference; and
    (5) executes a process, when the peak having the specified vibration amplitude or greater is detected in process (4), of replacing the arrival time of the maximum peak with the arrival time of that peak and calculating the difference in the process (1), and then executing processes (2) and (3).

2. The damage length measurement system according to claim 1, wherein
    the system has three or more vibration detection sensors, and
    the measurement apparatus is constructed such that:
    in process (1) it calculates the difference between the maximum peak of the vibration wave detected by a specified vibration sensor and the maximum peak of the vibration wave detected by each of the other vibrations sensors
    in process (2) it determines whether or not each difference is within the reference range; and
    in process (4), when none of the differences is within the reference range, for the specified vibration detection sensor, it detects a peak that arrived before the maximum peak and that has the specified vibration amplitude or greater.

3. A damage length measurement method for measuring a length of damage that occurred in an object being measured, the method comprising the steps of:

applying an ultrasonic vibration to the object by an oscillator;

detecting at mutually different positions a vibration wave that propagates through the object from the oscillator by a plurality of vibration detection sensors; and executing a measurement process of controlling the vibration of the oscillator, and analyzing the vibration wave that was detected by the vibration detection sensors by means of processing detected signals from the vibration detections sensors, wherein the measurement process:

(1) executes a process of calculating arrival times of maximum peaks of the vibration wave detected by at least two vibration detection sensors that are selected from the plurality of vibration detection sensors, and calculating a difference between the arrival times;

(2) executes a process, following process (1), of determining whether or not the difference between the selected sensors is within a set reference range considering a vibration propagation time between the at least two vibration sensors;

(3) executes a process, when it is determined in process (2) that the difference is within the reference range, of calculating the damage length based on a delay time with respect to a calibration value of the arrival times of the maximum peaks;

(4) executes a process, when it is determined in process (2) that the difference is not within the reference range, of detecting a peak arrived before the maximum peak and that has a specified vibration amplitude or greater for at least one of the at least two vibration detection sensor related to the difference; and (5) executes a process, when the peak having the specified vibration amplitude or greater is detected in process (4), of replacing the arrival time of the maximum peak with the arrival time of that peak and calculating the difference in the process (1), and then executing processes (2) and (3).

4. The damage measurement method according to claim 3, wherein the method uses three or more vibration detection sensors, and the measurement process:

in process (1) calculates the difference between the maximum peak of the vibration wave detected by a specified vibration sensor and the maximum peak of the vibration wave detected by each of the other vibrations sensors in process (2) determines whether or not each difference is within the reference range; and in process (4), when none of the differences is within the reference range, for the specified vibration detection sensor, detects a peak that arrived before the maximum peak and that has the specified vibration amplitude or greater.

\* \* \* \* \*